United States Patent
Piper

(10) Patent No.: US 11,014,874 B2
(45) Date of Patent: May 25, 2021

(54) SYSTEM AND METHOD FOR PRODUCING PROPYLENE AND ACRYLONITRILE FROM CARBON DIOXIDE AND ETHYLENE

(71) Applicant: Jeremiah Lee Piper, Baton Rouge, LA (US)

(72) Inventor: Jeremiah Lee Piper, Baton Rouge, LA (US)

( * ) Notice: Subject to any disclaimer, the term of this patent is extended or adjusted under 35 U.S.C. 154(b) by 0 days.

(21) Appl. No.: 16/983,258

(22) Filed: Aug. 3, 2020

(65) Prior Publication Data

US 2021/0053910 A1    Feb. 25, 2021

Related U.S. Application Data

(60) Provisional application No. 62/888,647, filed on Aug. 19, 2019.

(51) Int. Cl.
| | |
|---|---|
| *C07C 253/26* | (2006.01) |
| *C07C 1/04* | (2006.01) |
| *C07C 11/06* | (2006.01) |
| *C07C 255/08* | (2006.01) |

(52) U.S. Cl.
CPC .......... *C07C 253/26* (2013.01); *C07C 1/0485* (2013.01); *C07C 11/06* (2013.01); *C07C 255/08* (2013.01)

(58) Field of Classification Search
CPC .................................................. C07C 253/26
See application file for complete search history.

(56) References Cited

U.S. PATENT DOCUMENTS

| | | | | |
|---|---|---|---|---|
| 3,885,928 A | * | 5/1975 | Wu | C07C 253/34 95/193 |
| 9,834,497 B2 | * | 12/2017 | Shaikh | B01J 29/40 |
| 10,065,906 B2 | * | 9/2018 | Shaikh | B01J 37/0201 |

* cited by examiner

*Primary Examiner* — Golam M Shameem

(57) ABSTRACT

A system and method for efficiently and sustainably producing propylene and acrylonitrile is disclosed which utilizes biodegradable materials, combustible materials that produce carbon dioxide and/or carbon monoxide. According to one embodiment of the invention, a source of carbon dioxide and/or carbon monoxide is utilized and the carbon dioxide and/or carbon monoxide is electrochemically reduced to ethylene. Dimerization is applied to separate the ethylene to produce 1-butene; which is isomerized to produce 2-butene. The 2-butene is metathesized to produce propylene. The propylene may then be subject to ammoxidation as desired in order to produce acrylonitrile.

19 Claims, 4 Drawing Sheets

SYSTEM AND METHOD FOR PRODUCING PROPYLENE AND ACRYLONITRILE FROM CARBON DIOXIDE AND ETHYLENE

PRIORITY CLAIM

This application claims priority to provisional application No. 62/888,647, filed on Aug. 19, 2019.

BACKGROUND OF THE INVENTION

Field of the Invention

The general field of the invention is the production of petrochemical products, particularly that of propylene and acrylonitrile.

Description of the Related Art

Propylene is a petrochemical, derived from the refinement of petroleum. Chemically, it is an unsaturated organic compound ($C_3H_6$). Propylene is typically produced as a byproduct of steam cracking—a process that breaks down saturated hydrocarbons into smaller, unsaturated hydrocarbons. Propylene is primarily used to produce polypropylene, a plastic used in the manufacture of myriad products ranging from plastic bags and molding to piping systems and carpeting.

Acrylonitrile is an organic compound ($CH_2CHCN$) and a petrochemical in high demand. It is produced primarily by the catalytic ammoxidation of propylene, a process in which propylene, ammonia, and air are passed through a reactor containing a catalyst ($CH_3CH=CH_2 + 3/2 O_2 + NH3 \rightarrow NCCH=CH_2 + 3 H_2O$). Acrylonitrile is used to create polyacrylonitrile, ABS plastics, and acrylamide. Acrylonitrile is central to the production of many polymers and synthetic fibers, particularly carbon fibers. Because carbon fibers offer significant advantages, such as high tensile strength, high chemical and heat resistance, low weight, and low thermal expansion, they are superior to most other natural and manmade products. When combined with other materials, like plastic resin or graphite, the resulting composite has many industrial and commercial applications. In particular, carbon fibers are in highest demand in the aerospace, aircraft, automotive, and wind energy industries. But the production of acrylonitrile is dependent upon the supply of propylene, which is currently outstripped by demand. This imbalance has created a propylene supply gap, which in turn results in the current low supply, and high price, of acrylonitrile.

The propylene supply gap exists because there is no significant direct industrial scale production of propylene. While technologies for the direct production of propylene are available, they have yet to lower the price of propylene because they still rely on relatively expensive petroleum-derived feedstock. One example is propane dehydrogenation, whereby propane is heated to at least 1,000 degrees Fahrenheit, passed through a reactor containing a catalyst, and hydrogen and propylene are ultimately recovered. However, propane is derived from extraction of oil and natural gas, and is thus dependent on the supply and price of oil and natural gas. Yet the biggest drawback of propane dehydrogenation, or any industrial process that relies on fossil fuels, is the environmental cost.

Various United States Federal Agencies, as well as the Intergovernmental Panel on Climate Change of the United Nations, have established that burning fossil fuels is the primary cause of the ongoing climate change crisis. The severe and long-lasting negative impacts to every sector of life as we know it are well known. Warming oceans, rising sea levels, and extreme weather events alone are already altering food production and impacting trade, causing loss of habitat for humans and other species, and damaging infrastructure. Projections indicate millions of lives are at risk and that global gross domestic product will decrease by at least 2% to 10% each year.

For all these reasons, there is great demand for a sustainable and cost-effective way to close the propylene gap and bring a large supply of propylene and acrylonitrile to market.

SUMMARY OF THE INVENTION

The present invention provides a system and method for efficiently and sustainably producing propylene and acrylonitrile by changing the feedstock. By using biodegradable materials, combustible materials that produce carbon dioxide/carbon monoxide, and/or carbon dioxide/monoxide captured from the air, the present invention creates a sustainable and cost-effective system for producing propylene and acrylonitrile. Feedstock examples include but are not limited to: municipal solid waste; food waste; and carbon capture technologies. Unlike petroleum-based feedstocks, these feedstocks are inexpensive, sustainable, and comprise readily available sources of carbon dioxide. Consequently, use of these feedstocks will drive down production costs, increase supply, and reduce the price of propylene and acrylonitrile.

Additional benefits of the present invention include the ability to: (1) customize and upgrade the system to adapt to new technologies and/or the needs of the manufacturer by using various feedstock sources and component processes; and (2) use of a direct ethylene source as a buffer in the event sources of carbon dioxide are diminished or temporarily not available.

According to one embodiment of the invention, a source of carbon dioxide and/or carbon monoxide is utilized and electrochemically reduced to ethylene. Dimerization is applied to convert the ethylene to produce 1-butene; which is isomerized to produce 2-butene. The 2-butene is metathesized to produce propylene. The propylene is then subject to ammoxidation in order to produce acrylonitrile.

Further benefits and advantages of the invention, along with other illustrative embodiments, are set forth in the Detailed Description of the Invention.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The invention pertains to systems and methods of producing propylene and acrylonitrile. As described above, producing acrylonitrile can be difficult and expensive, often requiring input of non-renewable byproducts of oil and natural gas refining. This invention offers a new and advantageous method for generating acrylonitrile, which can be cost-effective and uses renewable inputs. This invention offers a process for direct conversion of carbon dioxide and/or carbon monoxide to acrylonitrile. This allows the invention to advantageously utilize renewable resources as fuel input. By using lower cost, renewable resources, and a combination of technologies previously not thought to be combined, the invention produces acrylonitrile for a reduced price at a heightened efficiency.

Figure 1:
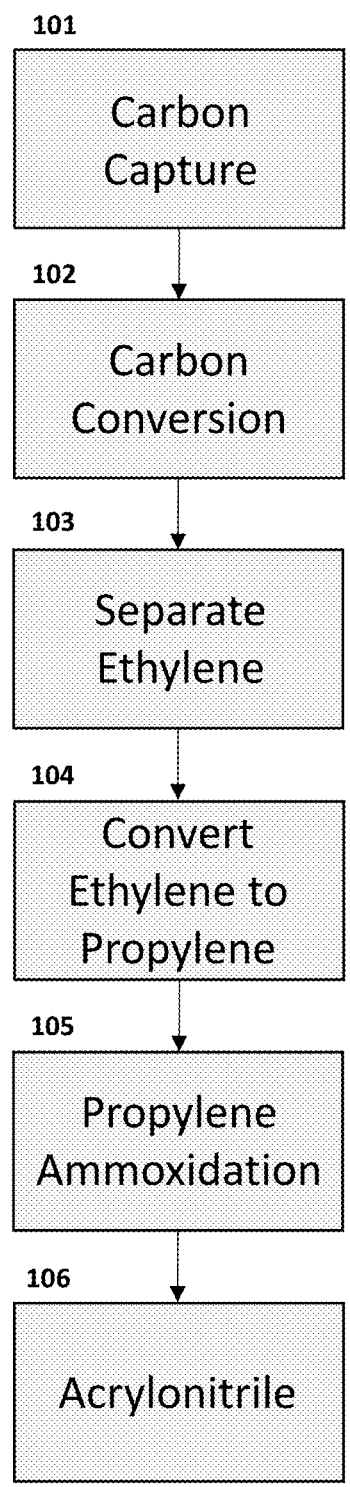
FIG. 1 depicts a flow diagram depicting an exemplary overview of the one embodiment of the inventive method.

In a preferred exemplary embodiment, and with reference to FIG. 1, at step 101 the invention uses source carbon from a variety of sources. Carbon dioxide or carbon monoxide can then be converted to ethylene using known carbon conversion technologies at step 102. In some embodiments, the carbon conversion technology comprises renewable methods. In some embodiments, conversion may use electrochemical reduction to convert readily available carbon dioxide or carbon monoxide from renewable sources into ethylene by use of electricity. Generation of ethylene from carbon dioxide and/or carbon monoxide may be performed via a variety of methods.

Because the invention uses carbon dioxide or carbon monoxide as an input, the invention may advantageously utilize a variety of carbon sources. In some embodiments, these sources of carbon may include renewable resources. In other embodiments, these sources of carbon may be from waste products generated by industrial, agricultural, or municipal sources. In other embodiments, these sources of carbon may be non-renewable sources. In some embodiments, the invention uses ethylene that is not generated via carbon conversion.

Returning to FIG. 1, once pure ethylene is separated at step 103 it is converted to propylene at step 104. In preferred embodiments, the conversion of ethylene to propylene occurs in a single system. Propylene is then ammoxidized at step 105, with the resulting output at step 106 being acrylonitrile. In preferred embodiments, the ammoxidation step 105 also takes place in the same system as the conversion to propylene step 104. That way, excess heat generated from the ammoxidation process may be used in the propylene conversion step.

In some embodiments, undesired byproducts of each step in the process can be cycled back into the overall system as a result of the use of carbon dioxide and monoxide as a feedstock, as both are the primary emissions of the combustion of many hydrocarbons. As these byproducts would typically be sold off to other companies, this process adds efficiency and lowers waste. In other embodiments, the combustion required to generate carbon dioxide or carbon monoxide can be utilized to generate power. This adds another point of efficiency to the invention. Another important aspect of the invention's efficiency is the use of ammoxidation's exothermic reaction and production of high-quality steam in the isomerization/metathesis reactions which in many forms require the use of high-power steam.

1. Carbon Conversion

Figure 2:
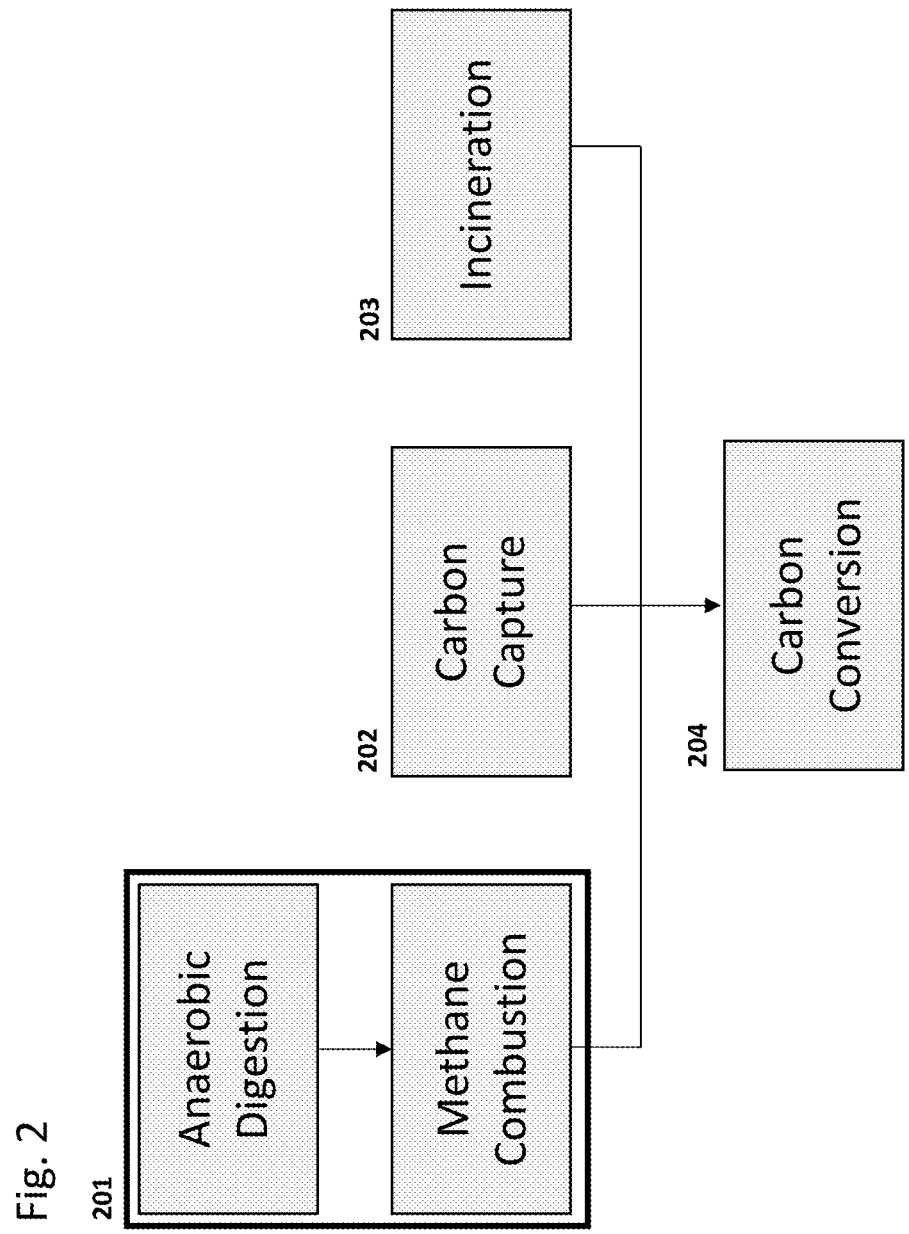
FIG. 2 depicts a flow diagram of one exemplary method that may be used to generate carbon dioxide according to one embodiment of the invention.

In preferred embodiments, and with reference to FIG. 2, the invention involves generation of hydrocarbons for purposes of producing acrylonitrile using carbon conversion technologies. Carbon conversion technologies refers to technologies whose main goal is to convert source carbon from carbon dioxide or carbon monoxide into usable hydrocarbons for industrial purposes. As depicted in FIG. 2, carbon conversion technologies may utilize carbon dioxide or carbon monoxide from a variety of sources, e.g. anaerobic digestion and methane combustion 201, conventional carbon capture 202, and/or via incineration processes 203. These different methods of carbon conversion are discussed in more detail below. Of course, these carbon conversion technologies are exemplary only, and any source of carbon may advantageously be used with the invention.

In one representative embodiment, carbon dioxide may be produced from anaerobic digestion of biodegradable materials 201, which are digested to produce carbon dioxide and methane. In this embodiment, methane and carbon dioxide are produced by microorganisms in an air-free environment by digestion of biomass. Examples of such microorganisms may include acetic acid-forming bacteria and methane-forming archaea.

Examples of carbon-containing compounds and materials include cellulose, lignin, rubber, and plastics. Examples of biomass can include crops, agricultural waste, food waste, municipal solid waste, municipal liquid waste, wood and/or wood waste, wood processing waste, sawdust, paper waste, and compost.

If methane is the product of this step, further combustion will be utilized to convert the methane into carbon dioxide or carbon monoxide. Alternatively, this methane can be used in a methane-powered turbine/generator, or used to power incineration of other carbon-containing compounds and materials such as those found in municipal solid waste.

In another representative embodiment, the carbon dioxide or carbon monoxide is captured directly from industrial systems, or from the surrounding environment such as the air or water 202. For example, industrial systems may include foundries, factories, biogas plants, and chemical plants.

In some embodiments, carbon dioxide or carbon monoxide is generated from incineration of other carbon-containing compounds 203. In some embodiments, carbon dioxide or carbon monoxide is generated from incineration of biomass. In other embodiments, carbon dioxide or carbon monoxide is generated from incineration during the normal operation of industrial processes. Examples may include coal power plants, natural gas power plants, oil power plants, or fossil fuel burning industrial processes. The carbon dioxide or carbon monoxide from these sources, as well as from sources not listed in the examples above, are stored and contained for use in processing of acrylonitrile.

Regardless of the source of carbon, the next step 204 of the process as shown in FIG. 2 is conversion of the carbon sources to low molecular weight hydrocarbons. In one embodiment, this process occurs via electrolytic reduction of carbon dioxide or carbon monoxide in the presence of water to produce hydrocarbons of low molecular weight, especially ethylene. This process occurs in, for example, an electrochemical reduction and carbon conversion unit. Electrolysis of carbon dioxide or carbon monoxide can be performed via methods that are known to persons skilled in the art. For example, electrolysis may be performed via a hydroxide-mediated copper catalysis. See, e.g., Dinh et al., Science 360, 783-787 (2018), $CO_2$ electroreduction to ethylene via hydroxide-mediated copper catalysis at an abrupt interface, which is incorporated by reference in its entirety for all purposes. In other embodiments, different catalysts may be used. See, e.g., R. Kas et al., Nat. Commun. 7, 10748

(2016); M. Liu et al., Nature 537, 382-386 (2016); C. Reller et al., Adv. Energy Mater. 7, 1602114 (2017); Y. Li et al., Nano Lett. 17, 1312-1317 (2017); P. De Luna et al., Nat. Catal. 1, 103-110 (2018), all of which are incorporated by reference in their entirety for all purposes.

Figure 4:
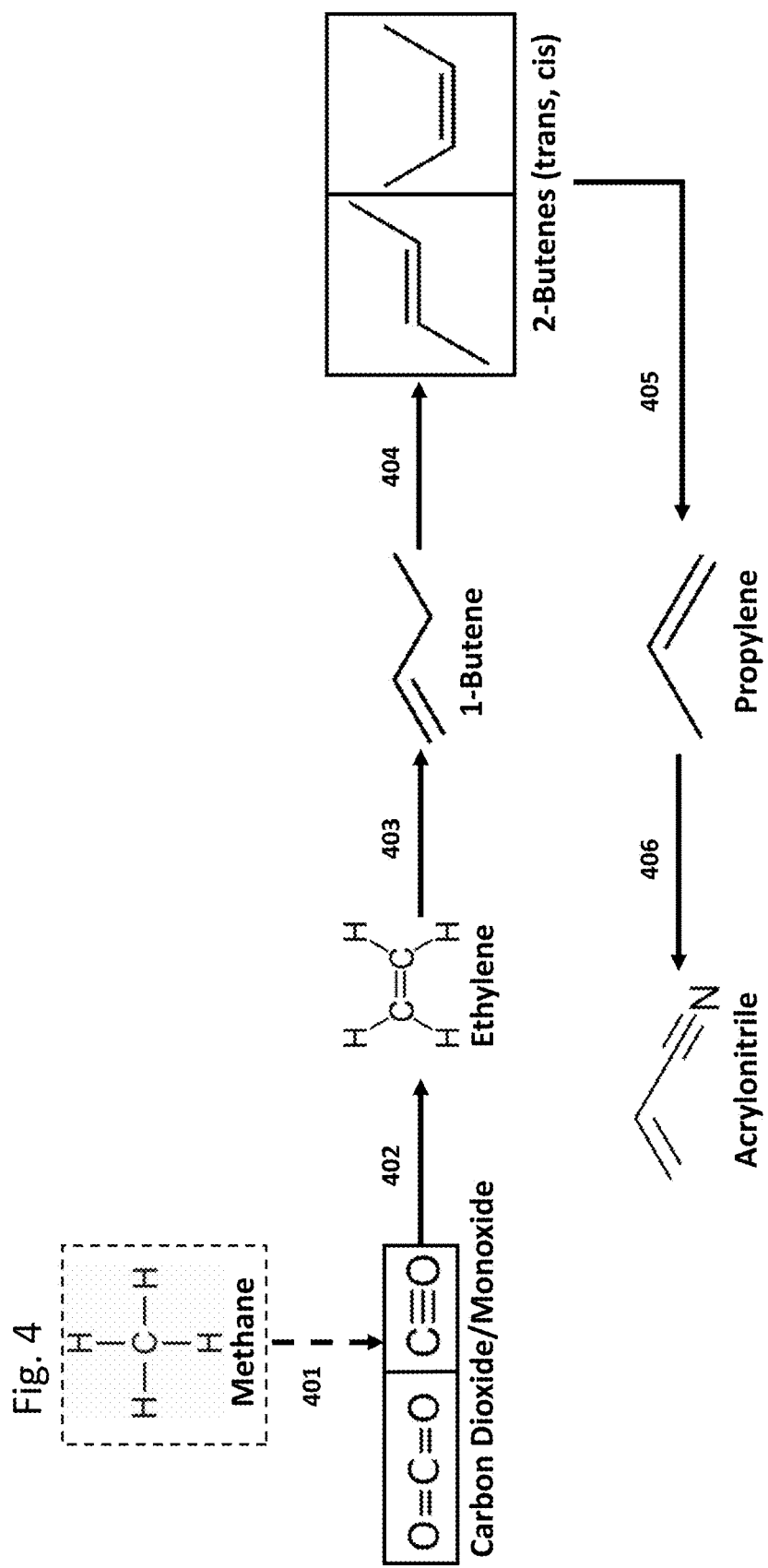
FIG. 4 depicts the chemical intermediates after each step of the acrylonitrile formation according to an exemplary embodiment of the invention.

In preferred embodiments, the primary product of carbon conversion is ethylene, as shown in FIG. 4 (showing that carbon dioxide or carbon monoxide is processed at step 402 to produce ethylene). In some embodiments, carbon conversion generates small molecule hydrocarbons other than ethylene, such as methane. Non-ethylene byproducts in the electrolysis reaction are filtered off. In some embodiments, non-ethylene byproducts may be further combusted to generate carbon dioxide, carbon monoxide, and/or power. In preferred embodiments, the carbon dioxide, carbon monoxide, and power generated from such combustion may then be further utilized in the system. That way, all mass entered into the system may be utilized for production of acrylonitrile, increasing the efficiency of the system. The ethylene produced in the preferred embodiments can then be stored for further use in the system.

2. Acrylonitrile Synthesis

Figure 3:
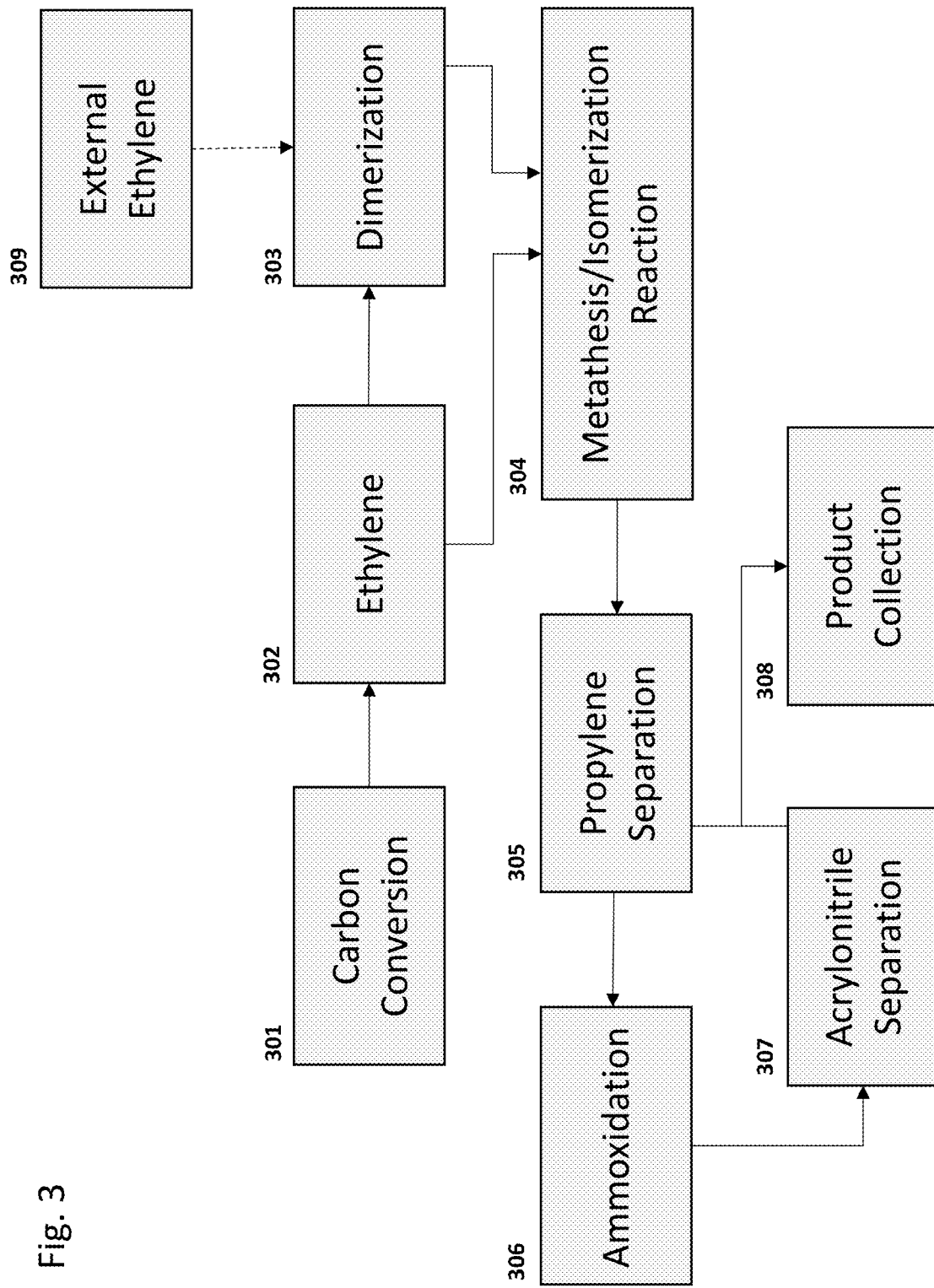
FIG. 3 depicts the chemistry steps used to generate acrylonitrile from carbon dioxide according to an exemplary embodiment of the invention.

In preferred embodiments and with reference to FIG. 3, this invention also includes methods to make acrylonitrile from carbon sources. Carbon conversion technologies at step 301 can be used to produce ethylene. Alternatively, ethylene can alternatively be made from the dehydration of ethanol. Once ethylene is produced or sourced, the invention advantageously produces acrylonitrile in a single contiguous process. If carbon conversion technology is utilized, ethylene may optionally be first separated from other hydrocarbon products as part of the conversion process at step 302. This separation can be performed using standard separation techniques.

Ethylene is then converted to propylene/propene. In a preferred embodiment, conversion of ethylene to propylene uses three steps: dimerization 303, and metathesis and isomerization 304.

In addition or alternatively to, the input for acrylonitrile synthesis may be ethylene generated from sources other than carbon conversion. For example, carbon conversion can be replaced or combined with the use of a direct ethylene source 309. For example, ethylene is a common byproduct of oil and natural gas extraction. In some embodiments, this additional ethylene source may comprise the primary source of ethylene. In other embodiments, this additional ethylene source may be used in tandem with earlier steps as a "buffer" in the event that a fully established ethylene source, such as from a carbon conversion system, cannot be maintained.

In preferred embodiments, ethylene is dimerized at step 303 in FIG. 3 to produce 1-butene (see step 403 in FIG. 4). Dimerization can be performed using methods known to those of skill in the art. See, e.g., U.S. Pat. No. 7,868,216, which is incorporated by reference in its entirety for all purposes. In some embodiments, dimerization can be performed using catalysts and methods such as Alphabutol®. See, Handbook of Petroleum Processing, Edited by D. S. J. Jones, P. R. Pujado; Springer Science 2008; Forestiere et al., Oil & Gas Science and Technology-Rev. IFP (2009); 64(6): 649-667.

Next, 1-butene is isomerized at step 304 in FIG. 3 to 2-butene (step 404 in FIG. 4) and subsequently metathesized to propylene (step 405 in FIG. 4). Butene isomerization and metathesis may be performed in any manner known in the art. In preferred embodiments, the steps of isomerization and metathesis are performed in a "one-pot" synthesis, where 1-butene is isomerized to 2-butene and metathesized to form propylene. See, e.g., U.S. Pat. Nos. 8,440,874, 6,777,582 which are both incorporated by reference in their entirety for all purposes. In other embodiments, the steps of isomerization and metathesis are separate steps. In some embodiments, metathesis utilizes ethylene generated from step 301 of the invention.

Following isomerization and metathesis, at step 305 in FIG. 3 propylene may be separated from by-products for further use according to existing methods. Byproducts of this process may be further combusted to generate carbon dioxide and carbon monoxide, which may then be used as further feedstock for the invention. Advantageously, this invention also provides for the synthesis of propylene from carbon conversion. Propylene produced could be separated and sold in and of itself if acrylonitrile is not the desired product, or if the means to enact ammoxidation are not at one's disposal.

Acrylonitrile itself is produced by the process of ammoxidation of propylene as shown at step 306. In preferred embodiments, ammoxidation of propylene to acrylonitrile is performed via known processes. See Callahan et. al., Ind. Eng. Chem. Prod. Res. Develop., Vol. 9, No. 2, 1970, Oxidation and Ammoxidation of Propylene over Bismuth Molybdate Catalyst, which is incorporated by reference in its entirety for all purposes. Ammoxidation is an exothermic reaction. Therefore, energy released by the ammoxidation process may be utilized to generate steam. Steam generated by this process may be used in any of the aforementioned processes which may require steam, such as in the metathesis/isomerization step.

Following ammoxidation, the final product is acrylonitrile at step 308. Acrylonitrile may then be used for further processing, e.g., in carbon fiber manufacture, or it may be stored and sold for other uses. In some instances, pure acrylonitrile can be obtained directly from the ammoxidation reaction. In other circumstances, acrylonitrile is separated from other products of the ammoxidation reaction using known acrylonitrile processes as shown in step 307.

FIG. 4 depicts a preferred embodiment showing the products of each step of the invention. Optionally, methane may be combusted to form carbon dioxide and carbon monoxide (step 401). Carbon dioxide and/or carbon monoxide, either formed as a product of combustion or direct capture is electrochemically reduced to produce ethylene (step 402). Ethylene is dimerized to form 1-Butene (step 403). 1-butene is isomerized into 2-butene (step 404), and 2-butene is reacted with ethylene in a metathesis reaction to produce propylene (step 405). Any variation of this metathesis/isomerization chain can be used such as is described above. Finally, if acrylonitrile is a desired product, propylene is sent into an ammoxidation reaction to produce acrylonitrile (step 406).

In some embodiments, combustible hydrocarbon byproducts taken from the system during the processes of separation throughout the system, such as methane, may be sent into the units performing the incineration or methane combustion steps to generate additional carbon dioxide or carbon monoxide and power output from a set input of materials. Energy produced from methane combustion may be used primarily as a power-source for the system and its components as well as for any operations the manufacturer might have. In some embodiments, conversion of 1-butene to propylene uses high-purity steam. This steam can be generated from the exothermic ammoxidation reaction, thereby advantageously capturing waste heat.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method for production of acrylonitrile, comprising the steps of:
utilizing a source of carbon comprising carbon dioxide and/or carbon monoxide;
converting through electrolytic reduction or electrochemical reduction of said carbon dioxide and/or carbon monoxide to ethylene;
dimerizing said ethylene by a catalytic process to produce 1-butene;
using a synthesis process to isomerize said 1-butene to produce 2-butene and to metathesize said 2-butene with ethylene to produce propylene; and
producing acrylonitrile by ammoxidation of said propylene.

2. The method of claim 1, wherein one or more of the conversion, isomerization, metathesis, and ammoxidation steps are performed in a one-pot synthesis.

3. The method of claim 1, wherein ethylene not generated by the conversion of carbon dioxide and/or carbon monoxide is input from another source.

4. The method of claim 1, wherein converting said carbon dioxide and/or carbon monoxide comprises electrochemical reduction of said carbon dioxide and/or carbon monoxide.

5. The method of claim 1, wherein converting said carbon dioxide and/or carbon monoxide utilizes renewable sources of electricity.

6. The method of claim 1, further comprising the step of anaerobic digestion of biodegradable materials, which produces said carbon dioxide and methane.

7. The method of claim 6, wherein methane generated during anaerobic digestion is used as a fuel source to power the other steps of the method.

8. The method of claim 6, wherein said carbon dioxide and said methane are produced by microorganisms in an air-free environment by digestion of biomass.

9. The method of claim 6, wherein said biomass comprises one or more of crops, agricultural waste, food waste, municipal solid waste, municipal liquid waste, wood waste, wood, wood processing waste, sawdust, paper waste, or compost.

10. The method of claim 6, further comprising a combusting step to convert said methane into additional carbon dioxide and/or carbon monoxide.

11. The method of claim 10, wherein the combusting step is utilized to generate power.

12. The method of claim 1, wherein the source of said carbon dioxide and/or carbon monoxide is one or more of industrial systems, air, or water.

13. The method of claim 1, further comprising the step of incinerating carbon-containing compounds as the source of said carbon dioxide and/or carbon monoxide.

14. The method of claim 13, wherein the carbon-containing compounds are found in biomass.

15. The method of claim 14, wherein said biomass comprises one or more of crops, agricultural waste, food waste, municipal solid waste, municipal liquid waste, wood waste, wood, wood processing waste, sawdust, paper waste, or compost.

16. The method of claim 12, wherein said industrial processes comprise those taking place at one or more of power generation processes.

17. The method of claim 1, wherein a byproduct generated by the method is steam, and wherein the steam is used in one or more of the isomerizing and metathesizing steps.

18. The method of claim 1, wherein metathesis of 2-butene further comprises utilizing ethylene produced via conversion of carbon dioxide and/or carbon monoxide.

19. The method of claim 1, wherein byproducts generated by each step is further combusted to generate carbon dioxide and/or carbon monoxide.

* * * * *